United States Patent [19]
Butler

[11] Patent Number: 5,119,132
[45] Date of Patent: Jun. 2, 1992

[54] DENSITOMETER AND CIRCUITRY WITH IMPROVED MEASURING CAPABILITIES OF MARKING PARTICLE DENSITY ON A PHOTORECEPTOR

[75] Inventor: Michael A. Butler, Rochester, N.Y.

[73] Assignee: Xerox Corporation, Stamford, Conn.

[21] Appl. No.: 605,058

[22] Filed: Oct. 24, 1990

[51] Int. Cl.⁵ .................................... G03G 15/00
[52] U.S. Cl. .................................... 355/208; 355/246; 355/326; 356/445; 250/205
[58] Field of Search ............ 355/246, 208, 326; 356/445, 446; 250/552, 553, 205; 118/688, 689, 691

[56] References Cited

U.S. PATENT DOCUMENTS

| | | | |
|---|---|---|---|
| 2,956,487 | 10/1960 | Giaimo, Jr. | 95/1.7 |
| 3,094,049 | 6/1963 | Snelling | 95/1.7 |
| 3,777,173 | 12/1973 | Landrith | 250/575 |
| 3,778,146 | 12/1973 | Knapp | 355/3 |
| 3,801,196 | 4/1974 | Knapp et al. | 355/3 |
| 3,801,349 | 4/1974 | Wilson et al. | 117/31 |
| 3,876,106 | 4/1975 | Powell et al. | 222/57 |
| 3,981,272 | 9/1976 | Smith et al. | 118/637 |
| 4,026,643 | 5/1977 | Bergman | 355/3 DD |
| 4,054,391 | 10/1977 | Witte | 356/209 |
| 4,082,445 | 4/1978 | Steiner | 355/14 |
| 4,178,095 | 12/1979 | Champion et al. | 355/14 R |
| 4,179,213 | 12/1979 | Queener | 355/14 R |
| 4,183,657 | 1/1980 | Ernest | 355/14 R |
| 4,226,541 | 10/1980 | Tisue | 356/446 |
| 4,284,356 | 8/1981 | Heilman | 356/429 |
| 4,312,589 | 1/1982 | Brannan et al. | 355/14 CH |
| 4,372,672 | 2/1983 | Pries | 355/14 R |
| 4,462,680 | 7/1984 | Ikeda | 355/14 D |
| 4,502,778 | 3/1985 | Dodge et al. | 355/14 E |
| 4,551,004 | 11/1985 | Paraskevopoulos | 355/3 DD |
| 4,553,033 | 11/1985 | Hubble, III et al. | 250/353 |
| 4,618,248 | 10/1986 | Buchar | 355/14 R |
| 4,684,243 | 8/1987 | Minor | 355/14 SH |
| 4,693,592 | 9/1987 | Karpan | 355/14 E |
| 4,796,065 | 1/1989 | Kanbayashi | 355/14 E |
| 4,799,082 | 1/1989 | Suzuki | 355/14 R |
| 4,801,980 | 1/1989 | Arai et al. | 355/14 D |
| 4,806,002 | 2/1989 | Simeth et al. | 356/445 |
| 4,829,336 | 5/1989 | Champion et al. | 355/246 |
| 4,833,506 | 5/1989 | Kuru et al. | 355/208 |
| 4,894,685 | 1/1990 | Shoji | 355/246 |
| 4,924,263 | 5/1990 | Bares | 355/208 |
| 4,950,905 | 4/1990 | Butler et al. | 250/358.1 |
| 4,962,407 | 10/1990 | Ueda | 355/208 |
| 4,965,634 | 10/1990 | Bando | 355/208 |
| 4,974,024 | 11/1990 | Bares et al. | 355/246 |
| 4,982,232 | 1/1991 | Naito | 355/208 |
| 4,999,673 | 3/1991 | Bares | 355/208 |
| 5,006,896 | 4/1991 | Koichi et al. | 355/246 |
| 5,019,859 | 5/1991 | Nash | 355/208 |

*Primary Examiner*—R. L. Moses

[57] ABSTRACT

The present invention relates generally to an electrographic apparatus and more specifically to an improved structural arrangement in electrographic apparatus of the type having a densitometer, which arrangement achieves improved measuring of marking particle density on a photoreceptor or the like. Wherein, use of a charge-coupled device (CCD) allows for a pixel-by-pixel recordation of the photo intensity reflected off of the photoreceptor and toner test patch. Therefore, as a result of the increased sensitivity of the toner measuring, it is possible to measure denser patches of toner, both black as well as color. Thus allowing for accurate monitoring of the amount of toner capable of being placed onto a photoreceptor.

34 Claims, 5 Drawing Sheets

DENSITOMETER AND CIRCUITRY WITH IMPROVED MEASURING CAPABILITIES OF MARKING PARTICLE DENSITY ON A PHOTORECEPTOR

BACKGROUND OF THE INVENTION

1. Field of the Invention

The present invention relates generally to an electrographic apparatus and more specifically to an improved structural arrangement in an electrographic apparatus of the type having a densitometer, which arrangement achieves improved measuring of marking particle density on a photoreceptor or the like.

2. Description of the Prior Art

It is known in the copying art to use light sensors to measure the density of a powderous substance or the like. The following patents are examples of similar devices, which are herein incorporated by reference where appropriate for appropriate teaching of additional or alternative details, features, and/or technical background. It is noted that the following descriptions are reliant upon excerpts from the identified patents, thus any inaccuracies in the following descriptions are a result of the patent's representation. For example, U.S. Pat. No. 4,806,002 discloses a densitometric sensing device in which a density measuring head, which is part of the device, traverses an ink test strip printed on a page which is fed to or placed on the device. The problem of misalignment between the placed ink test strip and the scanning direction of the density measuring head is avoided by providing a plurality of density measuring receivers in the measuring head, mounted transverse to the direction of travel so that the ink test strip is always under some of the receivers. The measured density values of all of the receivers are passed to a comparison circuit which cooperates with a logic circuit to determine from the values of the signals themselves which should be used to produce a composite density value, which is then used as the density for the zone being scanned.

U.S. Pat. No. 4,801,980, discloses the idea of using a toner density control apparatus constructed so that the toner density is controlled on the basis of the density. The density is detected by a sensor, of a patch image obtained by developing an image on a reference density plate on the surface of a photosensitive drum, characterized in that the apparatus includes means for controlling the rate of emission of a light from a light-emitting element in the sensor so that an output from a light receiving element, which is adapted to receive a light reflected on the surface of a non-image forming region of the photosensitive drum in the sensor, is in a predetermined level.

U.S. Pat. No. 4,551,004, discloses an apparatus for monitoring toner concentration on a photoreceptor surface. The apparatus includes a light emitting diode (LED), a phototransistor, a beam splitter and a lens disposed between the beam splitter and the photoreceptor surface to collimate the light beam between the lens and the photoreceptor surface. A portion of the light emitted from the LED is transmitted through the beam splitter and the lens to the photoreceptor surface. Collimated light is reflected from the photoreceptor surface back through the lens and reflected from the beam splitter to the phototransistor. The output signal from the phototransistor, because of the reflected collimated light beam, is not dependent upon the distance of the lens to the photoreceptor surface. Alternately, a second lens is disposed between the beam splitter and the phototransistor to enhance the overall resolution of the system.

Another example is U.S. Pat. No. 4,502,778, which discloses digital circuitry and microprocessor techniques to monitor the quality of toner operations in a copier and take appropriate corrective action based upon the monitoring results. Patch sensing is used. Reflectivity signals from the patch and from a clean photoconductor are analog-to-digital converted and a plurality of these signals taken over discrete time periods of a sample are stored. The stored signals are averaged for use in determining appropriate toner replenishment responses and/or machine failure indicators and controls.

U.S. Pat. No. 4,462,680 discloses a toner density control apparatus which assures always the optimum toner supply and good development with toner, irrespective of the kind or original to be copied and/or the number of copies to be continuously made. The apparatus has a detector for detecting the density of toner. The quantity of toner supply is controlled using a value variable at a changing rate different from the changing rate of the density difference between the reference toner density and the detected toner density.

U.S. Pat. No. 4,226,541 discloses illuminating a small area of a surface to be reflectively scanned, detecting the intensity of the light reflected from the small area and generating a first signal proportional thereto, detecting the intensity of the light reflected from an area at least partially surrounding the small area and generating a second signal proportional thereto, subtracting at least a fraction of the second signal from the first signal to produce a compensated signal which represents the reflectivity of the small area as compensated for the effects of scattered light, and either using the compensated signal directly as analog data or converting it to a digital output signal having a first state when the compensated signal is above a predetermined threshold and having a second state when the compensated signal is below that threshold.

In U.S. Pat. No. 4,178,095, a means exists to check for an abnormally low reflectance photoconductor during a test cycle in an electrophotographic copier machine by utilizing reflectivity sensing devices and circuitry ordinarily used for quality control where the reference signal is sensed from an area of the photoconductor normally used for document reproductions. This same means is also used for partially indicating correct circuit operation during machine operating periods when the circuit is not used for quality checking by a forced output condition not indicative of a quality check. This patent also discloses a means for producing a first signal which is a function of the reflectivity of the developer mixture, and means responsive to the number of replacement containers received by an interface means for producing an offset signal representing changes in developer mixture reflectivity caused by scanning of the carrier particles. Computation means such as a digital computer respond to the first signal and the offset signal to provide an accurate indication of the concentration of toner in the developer mixture.

U.S. Pat. No. 3,876,106 discloses an apparatus for continuously monitoring the concentration of toner in an electrographic developer mixture of toner and carrier particles at a magnetic brush development station by sensing the reflectivity of such mixture. The apparatus includes a radiation source for illuminating the mixture, first and second photocells for producing analog signals representative of the reflectivity of the mixture and the intensity of the radiation source, respectively. The apparatus further includes digital processing apparatus having an analog to digital converter and a programmable digital computer, having a stored program, which in response to the analog signals, produces in accordance with such stored program a representation of the relative proportion of toner particles in the mixture.

U.S. Pat. No. 3,777,173 discloses an apparatus for measuring the toner concentration in the developer of a xerographic copying apparatus. The measuring apparatus includes a toner collecting plate, and supply means for providing a stream of the developer containing the toner whose concentration is to be measured. The developer stream is directed onto a surface of the collecting plate to cause toner particles to be dislodged from the carrier beads, pellets or granules to which the toner particles are electroscopically adherent to deposit a layer of toner on at least a portion of the collecting plate. The developer stream removes toner from the collecting plate when the concentration of toner in the stream decreases. Means is provided for sensing the amount of toner deposited in the form of the aforementioned layer.

Lastly, U.S. Pat. No. 3,981,272 discloses the use of a sensor that senses that the toner concentration of the developer is below a predetermined set point level.

The ideal goal in xerography is to have the correct amount of toner deposited onto the photoreceptor on a continuous bases. Too little toner causes poor copy quality, too much toner causes excess wast and increased expense to run the system. Machines that can achieve this balance will have a tremendous competitive edge. Thus far, the use of a densitometer has been employed. However, the current densitometers either only work for black and white images, and not color, or are too simplistic in their ability to achieve higher resolution of the particles upon the photoreceptor or the like.

Therefore, in response to the problem, a need exists for a way to provide for both black and a high resolution color densitometer in a printer or copier.

As a result, the present invention provides a solution to the described problems and other problems, and also offers other advantages over the prior art.

SUMMARY OF THE INVENTION

The present invention comprises three main ideas. First, the invention comprises a densitometer including a reflectance sensor circuitry, adapted to receive light reflected from the member, comprising: means for receiving at least a portion of said reflected light, said receiving means generating a signal responsive thereto; a way for storing said signal generated by said receiving means; and a way for actuating said storage means to transmit said signal therefrom. Second, the invention involves an electrophotographic printing machine having a developer unit, toner, photoconductor charging and discharging devices, means for establishing toner test patches on a photoconductor, and a densitometer having a light source reflecting light on said photoconductor as said test patches move past said light source, and said densitometer having a reflectance sensor positioned so as to receive said reflected light, wherein said reflectance sensor includes: a way for receiving at least a portion of said reflected light, said receiving means generating a signal responsive thereto; a way for storing said signal generated by said receiving means; and a way for actuating said storage means to transmit said signal therefrom. Third, a method of measuring reflected light, including the steps of: receiving at least a portion of said reflected light, said receiving means generating a signal responsive thereto; storing said signal generated by said receiving means; and actuating said storage means to transmit said signal therefrom.

BRIEF DESCRIPTION OF THE DRAWINGS

In the drawings, like reference numerals indicate corresponding parts of preferred embodiments of the present invention throughout the several views, in which.

DETAILED DESCRIPTION OF THE PREFERRED EMBODIMENTS

I. Electrophotographic Printing Machine

Figure 1:
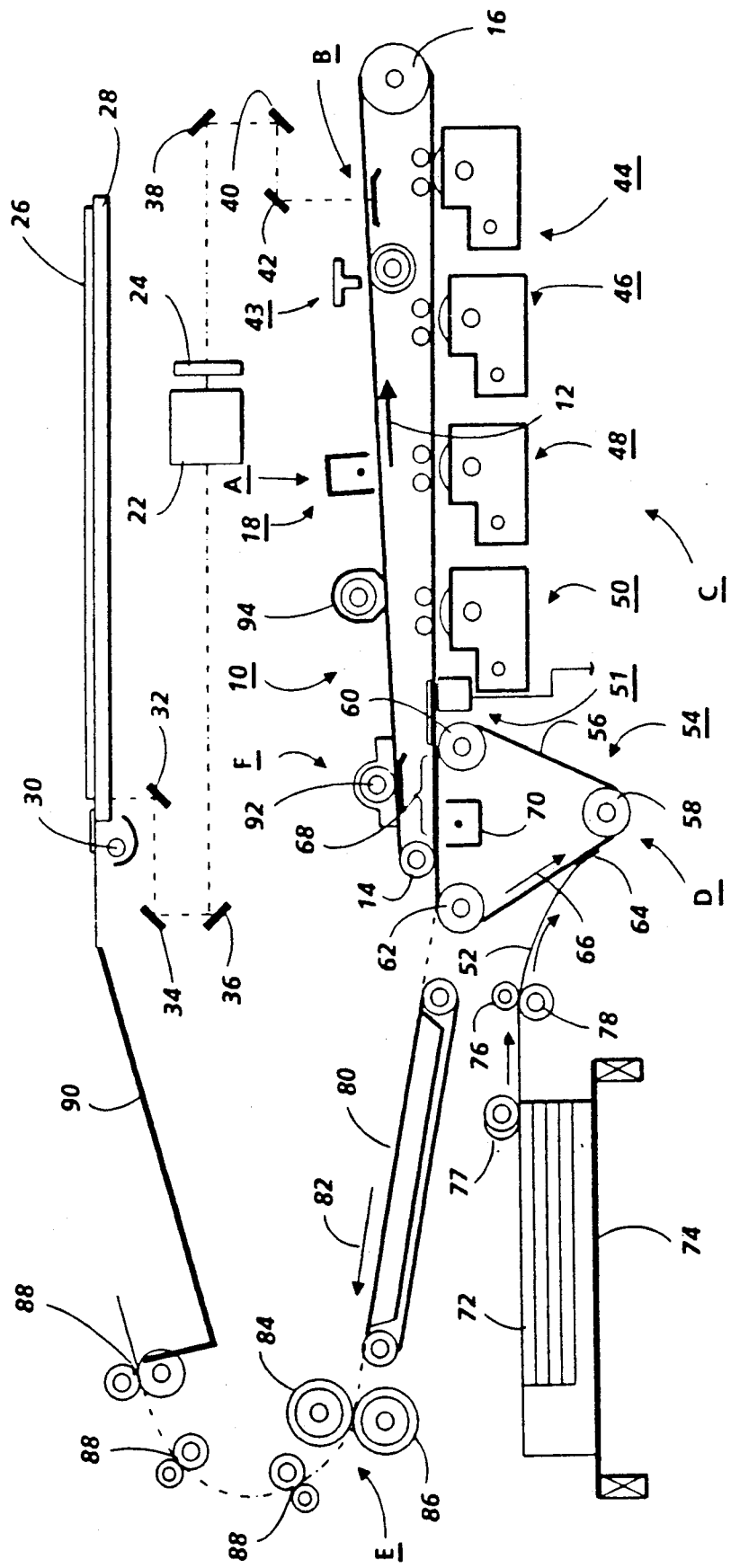
FIG. 1 is an electrophotographic printing machine.

Although specific terms are used in the following description for the sake of clarity, these terms are intended to refer only to the particular structure of the invention selected for illustration in the drawings, and are not intended to define or limit the scope of the invention.

For a general understanding of the features of the present invention, reference is made to the drawings. In the drawings, like reference numerals have been used throughout to designate identical elements. FIG. 1 schematically depicts the various components of an illustrative electrophotographic printing machine incorporating the infrared densitometer of the present invention therein. It will become evident from the following discussion that the densitometer of the present invention is equally well suited for use in a wide variety of electrostatographic printing machines, and is not necessarily limited in its application to the particular electrophotographic printing machine shown herein.

Inasmuch as the art of electrophotographic printing is well known, the various processing stations employed in the FIG. 1 printing machine will be shown hereinafter schematically and their operation described briefly with reference thereto.

As shown in FIG. 1, the electrophotographic printing machine employs a photoreceptor, i.e. a photoconductive material coated on a grounding layer, which, in turn, is coated on an anti-curl backing layer. The photoconductive material is made from a transport layer coated on a generator layer. The transport layer transports positive charges from the generator layer. The generator layer is coated on the grounding layer. The transport layer contains small molecules of di-m-tolydiphenylbiphenyldiamine dispersed in a polycarbonate. The generation layer is made from trigonal selenium. The grounding layer is made from a titanium coated Mylar. The grounding layer is very thin and allows light to pass therethrough. Other suitable photoconductive materials, grounding layers, and anti-curl backing layers may also be employed. Belt 10 moves in the direction of arrow 12 to advance successive portions of the photoconductive surface sequentially through the various processing stations disposed about the path of movement thereof. Belt 10 is entrained about idler roller 14 and drive roller 16. Idler roller 14 is mounted rotatably so as to rotate with belt 10. Drive roller 16 is rotated by a motor coupled thereto by suitable means such as a belt drive. As roller 16 rotates, it advances belt 10 in the direction of arrow 12.

Initially, a portion of photoconductive belt 10 passes through charging station A. At charging station A, a corona generating device, indicated generally by the reference numeral 18, charges photoconductive belt 10 to a relatively high, substantially uniform potential.

Next, the charged photoconductive surface is rotated to exposure station B. Exposure station B includes a moving lens system, generally designated by the reference numeral 22, and a color filter mechanism, shown generally by the reference numeral 24. An original document 26 is supported stationarily upon transparent viewing platen 28. Successive incremental areas of the original document are illuminated by means of a moving lamp assembly, shown generally by the reference numeral 30. Mirrors 32, 34 and 36 reflect the light rays through lens 22. Lens 22 is adapted to scan successive areas of illumination of platen 28. The light rays from lens 22 are transmitted through filter 24 and reflected by mirrors 38, 40 and 42 on to the charged portion of photoconductive belt 10. Lamp assembly 30, mirrors 32, 34 and 36, lens 22, and filter 24 are moved in a timed relationship with respect to the movement of photoconductive belt 10 to produce a flowing light image of the original document on photoconductive belt 10 in a non-distorted manner. During exposure, filter mechanism 24 interposes selected color filters into the optical light path of lens 22. The color filters operate on the light rays passing through the lens to record an electrostatic latent image, i.e. a latent electrostatic charge pattern, on the photoconductive belt corresponding to a specific color of the flowing light image of the original document. Exposure station B also includes a test patch generator, to provide toner test patches, indicated generally by the reference numeral 43, comprising a light source to project a test light image onto the charged portion of the photoconductive surface in the inter-image or inter-document region, i.e. the region between successive electrostatic latent images recorded on photoconductive belt 10, to record a test area. The test area, as well as the electrostatic latent image recorded on the photoconductive surface of belt 10, are developed with toner particles at the development stations. A test patch is usually electrostatically charged and developed with toner particles to the maximum degree compatible with the dynamic range of the monitoring sensor so as to monitor as much of the process as practicable.

After the electrostatic latent image and test area (or test patch) have been recorded on belt 10, belt 10 advances them to development station C. Station C includes four individual developer units generally indicated by the reference numerals 44, 46, 48 and 50. The developer units are of a type generally referred to in the art as "magnetic brush development units." Typically, a magnetic brush development system employs a magnetizable developer material including magnetic carrier granules having toner particles adhering triboelectrically thereto. The developer material is continually brought through a directional flux field to form a brush of developer material. The developer particles are continually moving so as to provide the brush consistently with fresh developer material. Development is achieved by bringing the developer material brush into contact with the photoconductive surface. Developer units 44, 46 and 48, respectively, apply toner particles of a specific color, which corresponds to the compliment of the specific color, onto the photoconductive surface. The color of each of the toner particles is adapted to absorb light within a preselected spectral reflection of the electromagnetic wave spectrum corresponding to the wave length of light transmitted through the filter. For example, an electrostatic latent image formed by passing the light image through a green filter will record the red and blue portions of the spectrums as an area of relatively high charge density on photoconductive belt 10. Meanwhile, the green light rays will pass through the filter and cause the charge density on the belt 10 to be reduced to a voltage level insufficient for development. The charged areas are then made visible by having developer unit 44 apply green absorbing (magenta) toner particles onto the electrostatic latent image recorded on photoconductive belt 10. Similarly, a blue separation is developed by developer unit 46, with blue absorbing (yellow) toner particles, while the red separation is developed by developer unit 48 with red absorbing (cyan) toner particles. Developer unit 50 contains black toner particles and may be used to develop the electrostatic latent image formed from a black and white original document. The yellow, magenta and cyan toner particles are diffusely reflecting particles.

Each of the developer units is moved into and out of an operative position. In the operative position, the magnetic brush is closely adjacent to belt 10, while, in the non-operative position, the magnetic brush is sufficiently spaced therefrom. During development of each electrostatic latent image, only one developer unit is in the operative position, the remaining developer units are in the non-operative position. This insures that each electrostatic latent image, and successive test areas, are developed with toner particles of the appropriate color without commingling. In FIG. 1, developer unit 44 is shown in the operative position with developer units 46, 48 and 50 being in the non-operative position. The developed test area passes beneath an infrared densitometer, indicated generally by the reference numeral 51. Infrared densitometer 51 is positioned adjacent the surface of belt 10 to generate electrical signals proportional to the amount of developed toner mass of the test area. The detailed structure of densitometer 51 will be described hereinafter with reference to FIGS. 2 through 6, inclusive.

After development, the toner image is moved to transfer station D, where the toner image is transferred to a sheet of support material 52, such as plain paper amongst others. At transfer station D, the sheet transport apparatus, indicated generally by the reference numeral 54, moves sheet 52 into contact with belt 10. Sheet transport 54 has a pair of spaced belts 56 entrained about three rolls 58, 60 and 62. A gripper 64 extends between belts 56 and moves in unison therewith. Sheet 52 is advanced from a stack of sheets 72 disposed on tray 74. Feed roll 77 advances the uppermost sheet from stack 72 into a nip, defined by forwarding rollers 76 and 78. Forwarding rollers 76 and 78 advance sheet 52 to sheet transport 54. Sheet 52 is advanced by forwarding rollers 76 and 78 in synchronism with the movement of gripper 64. In this way, the leading edge of sheet 52 arrives at a preselected position to be received by the open gripper 64. The gripper 64 then closes securing the sheet thereto for movement therewith in a recirculating path. The leading edge of the sheet is secured releasably by gripper 64. As the belts move in the direction of arrow 66, the sheet 52 moves into contact with belt 10, in synchronism with the toner image developed thereon, at transfer zone 68. Corona generating device 70 sprays ions onto the backside of the sheet so as to charge the sheet to the proper magnitude and polarity for attracting the toner image from photoconductive belt 10 thereto. Sheet 52 remains secured to gripper 64 so as to move in a recirculating path for three cycles. In this way, three different color toner images are transferred to sheet 52 in superimposed registration with one another. Thus, the aforementioned steps of charging, exposing, developing, and transferring are repeated a plurality of cycles to form a multi-color copy of a colored original document.

After the last transfer operation, grippers 64 open and release sheet 52. Conveyor 80 transports sheet 52, in the direction of arrow 82, to fusing station E where the transferred image is permanently fused to sheet 52. Fusing station E includes a heated fuser roll 84 and a pressure roll 86. Sheet 52 passes through a nip defined by fuser roll 84 and pressure roll 86. The toner image contacts fuser roll 84 so as to be affixed to sheet 52. Thereafter, sheet 52 is advanced by forwarding roll pairs 88 to catch tray 90 for subsequent removal therefrom by the machine operator.

The last processing station in the direction of movement of belt 10, as indicated by arrow 12, is cleaning station F. A rotatably mounted fibrous brush 92 is positioned in cleaning station F and maintained in contact with belt 10 to remove residual toner particles remaining after the transfer operation. Thereafter, lamp 94 illuminates belt 10 to remove any residual charge remaining thereon prior to the start of the next successive cycle.

II. Densitometer

In review, xerographic marking engines use a wide variety of internal sensors to maintain process stability. One such sensor is a developability sensor, also known as a densitometer, used to monitor the developed toner mass per unit of area (DMA) of substrate. Current developability sensors are optically based. The sensors are required to monitor the DMA of both black and colored toners.

Figure 2:
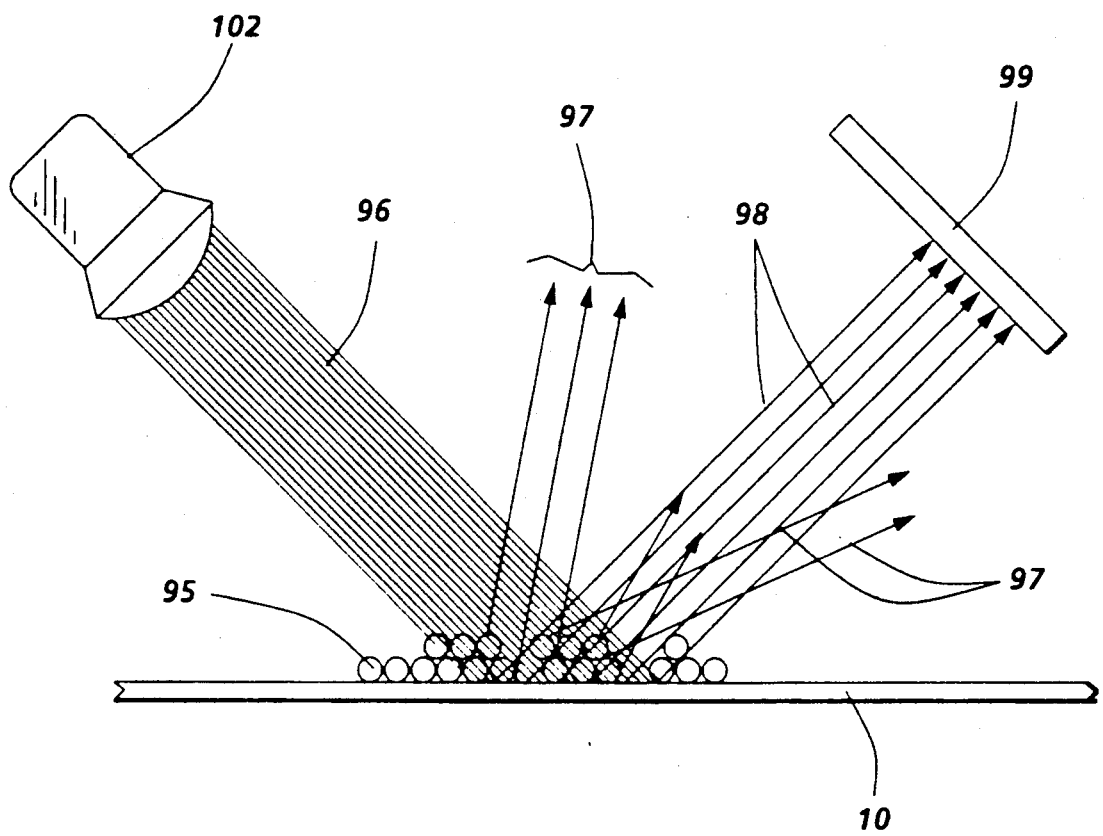
FIG. 2 is a schematic of a simplified densitometer.

Turning to FIG. 2, the following is a review of the principles of operation of a typical sensor. The sample is illuminated with a collimated beam of light 96 from an infrared LED 102 where the light is broken into three portions before being sensed by light receptor 99. First, there is light that is specularly 98 reflected from the substrate or photoreceptor belt 10. Then there is the light that is diffusely 97 reflected from both substrate 10 and toner particles 95. Finally, there is the light that is absorbed by the toner particles (mostly black toner). As the surface of the substrate 10 is covered with toner 95 the intensity of the light specularly reflected 98 from the substrate 10 is attenuated, yielding a small specular signal. The attenuation is the result of either absorption of the incident light 96, in the case of black toners, or scattering of the incident light 96 away from the specular reflection angle in the case of colored toners. The intensity of the diffusely reflected light 97 will increase for colored toners residing upon substrates such as a photoreceptor 10. This results from the scattering of the infrared radiation by the colored toner, and the weak absorption properties of the toner in the infrared.

Figure 3:
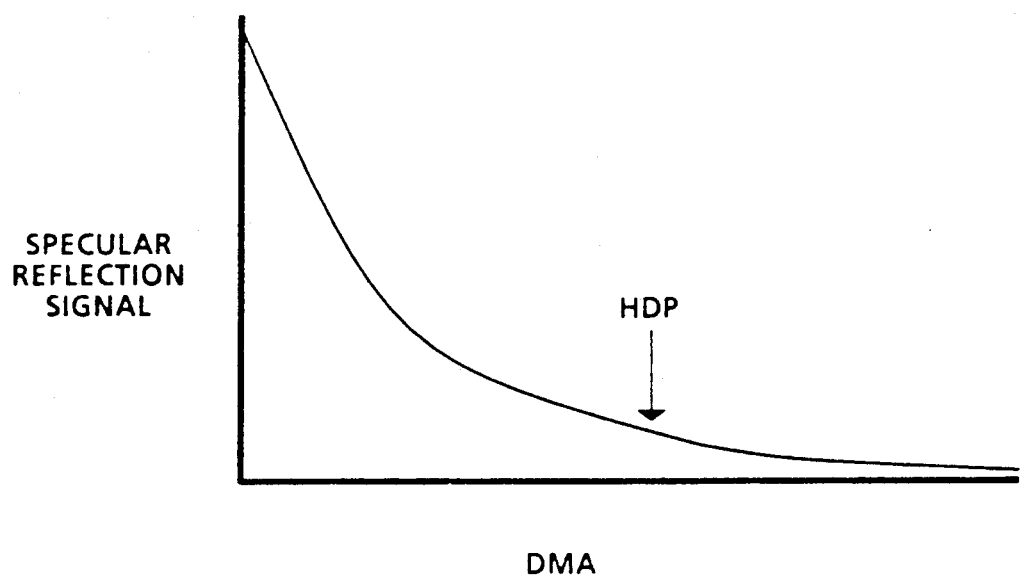
FIG. 3 is a graph showing specular reflection signal versus density per mass of toner area.

As shown in FIG. 3, there is a relationship between the DMA and specular signal reflected by the belt 10. At a high DMA value, there is only a very small specular signal, as shown by the high density patch (HDP) location. It is noted further, large changes in high DMA values only results in a small change in the specular signal. Typical sensor designs heretofore have not been able to measure these small values with the requisite sensitivity. Moreover, measurements reaching above the HDP are required as well.

It has been shown that for colored toners residing upon photoreceptors, the full range of DMA values used in printing can be monitored with a diffuse reflectance measurement. Diffuse reflection sensing, however, will not work with black toner and measurement of the DMA for black toner will require a specular reflection measurement. For this reason, as well as for calibration purposes, a general purpose sensor will be required to have both a diffuse and a specular reflection detector. Conventional specular reflection sensing however, has a limited sensing range relative to the DMA requirements for printing. Although diffuse reflection sensing has a greater sensing range, calibration of a specular reflection sensor for black toner is much easier.

To achieve greater mounting latitude (placement of the sensor in a proper coordinate location and with proper parallelism with respect to the photoreceptor) of a developability sensor the senor uses a large aperture relative to the incident beam spot size. As a consequence when used with colored toners, the specular reflection detector collects both specular and diffuse light, as seen in FIG. 2. At low DMA's, relative to the maximum black toner DMA that can be discriminated against, the sensor loses sensitivity as a result of the increased flux of diffusely reflected light. To remedy this situation past toner area coverage (TAC) sensors have used two additional photodiodes which collect only the diffuse flux. A differential measurement between the two types of detectors subtracts the diffuse contributions from the specular detector signal. This technique, though adequate for many applications, is limited in sensitivity as well as having difficult mounting latitude since precise placement of the sensor is required.

In the present invention, a CCD (charge coupled device) is used as the imaging element to replace the conventional large-area single-site imaging elements in the developability sensor. The CCD, also identified as a reflectance sensor, is used to collect both the specular peak and enough of the diffuse flux at scattering angles immediately adjacent to the specular reflection angle to permit an accurate measurement of both the specular reflection peak and the diffuse flux.

In this scheme, the LED is pulsed, and during this period the CCD collects the image of the light reflected from the toner/substrate sample or test patch. The elements from the CCD are read out and digitized to be analyzed using digital signal processing algorithms implemented upon a microprocessor executing programs stored in onboard ROM. The specular peak should be easily filtered from the diffuse flux as a result of the higher spatial frequency content of the signal. Digital filtering algorithms are mature and well suited to this task.

For example, retaining the full 60 dB dynamic range of a typical CCD requires eight bits of digital information from each pixel in the CCD. Assuming for arguments sake, a 64 × 64 element CCD array, and a desire to complete the calculation in one second, the digitization rate is only 4 kHz. Assuming a sixth order finite impulse response filter implies a memory requirement of about 37 kbits. Also assuming a sixth order filter the microprocessor will need to run at 5 MHz to complete the calculation in one second. These are all easily achieved with current technology. Although, one skilled in the art will appreciate that this example is meant to demonstrate the technical feasibility. Although the spirit of the example is correct, it is a rough calculation. The microprocessor described is much less powerful than the TMS320C30 that is described hereinbelow. The TMS could do some of the Z-transform and FFT calculations that would not be feasible with the smaller micro described in this example.

The following is a more specific description of a charge coupled device or CCD, although other designs will also work. A CCD is a monolithic silicon structure in which discrete packets of electronic charge are transported from position to position by sequential clocking of an array of gates. The charge packets are minority carriers or electrons with respect to the p-type semiconductor substrate. In a receiving means, image photons pass through a transparent polycrystalline silicon gate structure and are absorbed in the silicon crystal structure creating hole-electron pairs. The resulting photoelectrons are collected in photosites during an integration period. In a generating means of the CCD, the amount of charge accumulated in each photosite is a linear function of the localized incident illumination intensity and the integration period, thus forming charge packets, which are also referred to as storage means. An interline transfer architecture of the CCD, also referred to as transport means, provides information in two sequential fields. At the end of an integration period, when the photogate voltage is lowered and the clock is high, charge packets from odd numbered photosite rows are transferred to the vertical transport registers to initiate an odd field readout. Clocking transports the charge packets up the vertical transport registers where they are transferred line by line into the horizontal output register. After readout of the odd field, the voltage is again lowered and the clock is high causing transfer of charge packets from even numbered photosite rows into the vertical registers, thereby initiating an even field readout. These charge packets are the basis of the analysis for separating the specular and diffuse reflected light or photons which in turn is the basis for monitoring the toner application process. An example of a CCD is described in U.S. Pat. No. 4,450,484 issued to Terakawa et al. in 1984 which is herein incorporated by reference.

III. Electronic Circuitry

Figure 4:
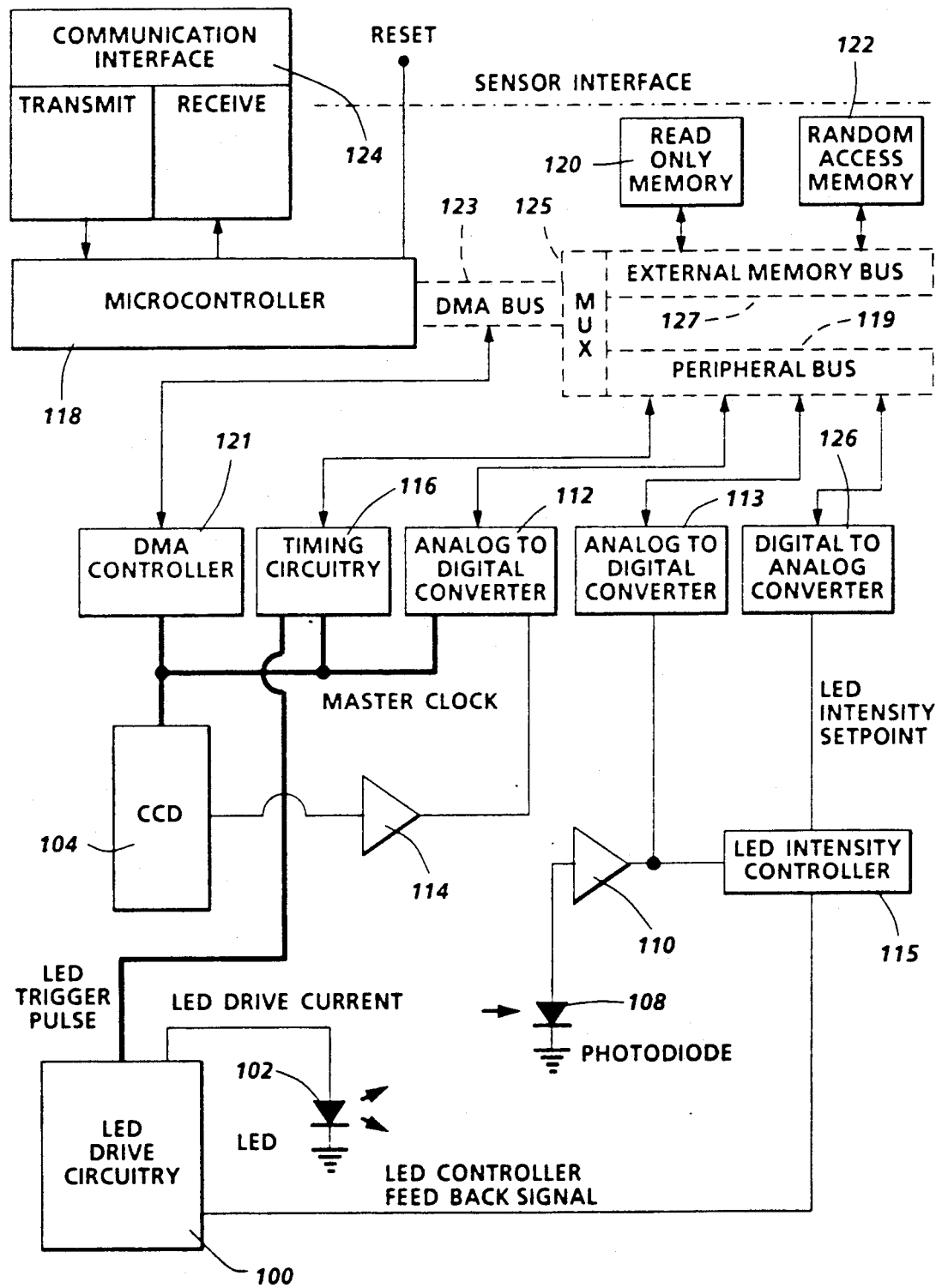
FIG. 4 is a block diagram of the densitometer circuitry.
Figure 6:
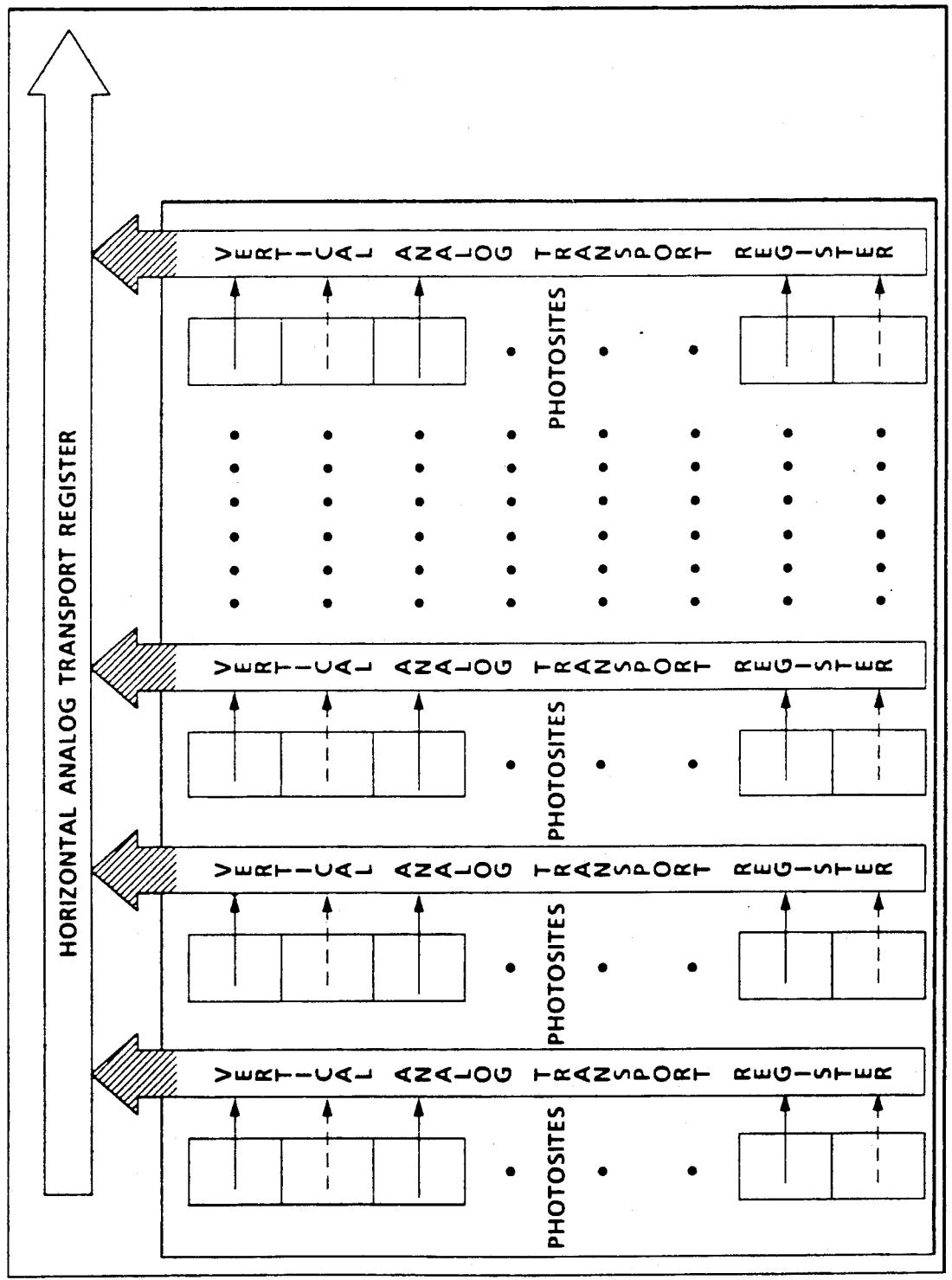
FIG. 6 is a representation of a charge coupled device.

With reference to FIG. 4, in accordance with the present invention there is shown a block diagram of the control circuitry for the densitometer. In particular, there is an LED drive circuit 100 for powering the LED 102. There are two light intensity receptors, a CCD 104 and photodiode 108. Photodiode 108 is connected to an appropriate amplifier 110, which in turn is linked to an analog to digital converter (A/D) 113 and an LED intensity controller 115. CCD 104 is coupled to an appropriate amplifier 114, which in turn is coupled to A/D converter 112. An example of a CCD is described in U.S. Pat. No. 4,450,484 issued to Terakawa et al. in 1984 which is herein incorporated by reference.

Timing circuitry 116, is in communication with CCD 104. Timing circuitry 116 controls the master clocking of the CCD and is in communication with, and controls when to pulse the LED drive circuitry 100.

Microcontroller (MC) 118 is linked to all other components through a direct memory access (DMA) controller 121, by way of a DMA bus 123. A Multiplexer 125, symbolized by MUX, switches information moving to and from the MC 118 to either peripheral bus 119 or external memory (EM) bus 127. EM bus 127 is connected to a read only memory (ROM) 120, which stores the programming for the densitometer's operation. Next, MC 118 is linked, via external memory bus 127 and the DMA bus 123, to a random access memory (RAM) 122, which stores the variables and data used by MC 118.

A/D converters 112 and 113 are linked to the MC 118 through peripheral bus 119. Similarly, digital to analog converter (D/A) 126 is connected to both MC 118 via the peripheral bus 119 and to LED intensity controller 114.

The final link to MC 118 is communication interface 124, which is connected to the master program that initiates and then responds to the whole densitometer test patch operation. Communication interface 124 consists of a transmit channel and a receive channel. Also provided is a reset connection for MC 118. An example commercially available for the main computer is the Digital Signal Processor (DSP) developed by Texas Instruments, the TMS320C30.

IV. Operation of the Densitometer

The following is a description of the operation of the densitometer in relation to the electrical block diagram. A signal, requesting that a toner patch measurement be performed, originates from a master computer (not shown). MC 118 receives the signal through the "receive" communications interface 124. Upon receiving the signal, MC 118 initiates a program, stored in ROM 120 which governs the operation of the sensor. From previous calculations or measurements, a digital setpoint is applied to D/A 126. This signal is then transformed to an analog value through D/A 126 for use by LED intensity controller 114. Afterwards, MC 118 issues a start of operation signal to timing circuitry 116. Whereupon, timing circuitry 116 performs the following steps: First, it initializes the CCD. Second, it activates the CCD. Finally, it issues an LED trigger pulse to LED drive circuitry 100. It is noted that LED 102 is activated for the duration of the trigger pulse. The LED intensity controller 114 stabilizes the LED 102 drive current at a value controlled by the set point provided by D/A 126.

Once the LED is activated it emits an infrared radiation in a narrowly defined beam through a lens, or other collimating device, onto the toner covered photoreceptor. This beam is both specularly and diffusely reflected by the toner covered photoreceptor sample, also known as a test patch. A lens or aperture is positioned so as to image the specularly reflected light onto CCD 104. The light collection system is designed to collect a substantial portion of diffusely reflected light emitted near to the specular reflection angle.

During the pulse of LED 102, the signal coming from amplifier 110, as a result of the monitoring of photodiode 108, is continuously digitized by A/D 113. The digitized information is stored by MC 118 to provide an integrated measurement of the photodiode current during the LED pulse. Photodiode 108 is positioned internal to the sensor in such a manner as to monitor the LED intensity. Therefore, the integrated photodiode response is a measure of LED 102 light flux during the sensor pulse.

With this information from A/D 113, the intensity of LED 102 can be adjusted from test sample run to run. Specifically, the signals received by photodiode 108 are used as a feedback signal which compensates and/or allows for the actual LED intensity that was measured during the LED pulse. This feedback signal is provided so that an optimum light intensity, equal to or greater than an LED intensity set point previously used, can be received by CCD 104. This is accomplished through D/A converter 126 which takes the digital signals from MC 118 and converts them to analog information for use by LED intensity controller 115. This digital signal is similar to the CCD digital signal in that it is a stepping digital function of time and luminosity, thus recording and converting the analog signal to an appropriate digital signal from a range of digital signals. LED intensity controller 115 provides an appropriate feedback signal to LED drive circuitry 100 which in turn determines the intensity of LED 102 during the next LED trigger pulse. Thus, this feedback signal is used to vary the light intensity produced by the LED 102 in order to optimize the specular information received from CCD 104. This adjustment is particularly useful when a particular light intensity only produces a small specular peak reading, often too small for prior art sensors to differentiate over diffusely reflected light. Wherein, by increasing the next toner test patch run by a certain percentage the specular light peak will also increase proportionately. Thus, providing for easier detection of the specular flux from the diffuse flux. This adjustment also works in reverse. Namely, if the light intensity set point results in an LED pulse that produce too much light, the CCD 104 or the amplifier 114 response will fail to be proportional to the amount of collected light, resulting in invalid data for that measurement. To remedy the large amount of light received, the next toner test patch run will be programmed to use less intensity. At the completion of the LED pulse, timing circuitry 116 deactivates CCD 104 and signals MC 118 that the LED pulse has finished.

Once the LED pulse sequence is finished, DMA controller 121 directs the data from CCD 104 to be transferred to A/D 112 where it is furthered to RAM 122. To do this, timing circuitry 116 is initialized to generate a typical clocking sequence for collection of the image stored at each photosite located on the CCD. Specifically, packets of charge, located at each pixel site (or photosite) in the CCD, are sequentially clocked out and amplified in charge sensitive amplifier 114. These charge packets are digitized and transferred via DMA transfer to RAM 122.

Figure 5:
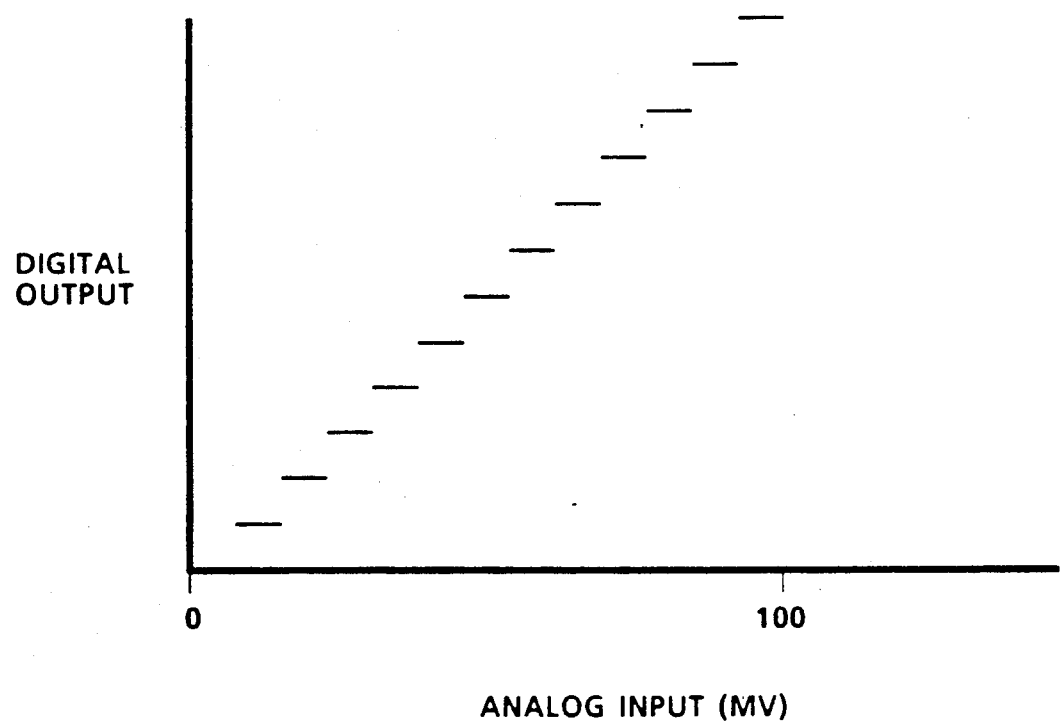
FIG. 5 is a graph showing the relationship of the digital output to the analog input in milivolts.

Referring now to A/D converter 112, which digitizes CCD 104 information, FIG. 5 demonstrates that for a continuous analog input signal a discrete stepping digital output signal results. Specifically, for each photosite on CCD 104 a particular digital value is selected from the whole digital range for storing into the RAM 122. Thus, a detailed measurement of the spatial variation of the light intensity pattern formed upon the detection element is made, and stored into RAM 122 for later analysis. This is a key concept of the invention. The location of the specular peak upon the detection element may vary from measurement to measurement as a result of fluctuations in the position of the photoreceptor that are inherent to the high speed motion of that device. Also, the location of the specular peak upon the detection element will vary from sensor to sensor as a result of sensor mounting variations from machine to machine. It is possible to ensure that the specular peak will always be captured by the specular detection element by the use of a single, large photodetector. The disadvantage of this method results from the need to compensate the measurement of the composite specular and diffuse signal that is actually detected for the diffuse signal. This is typically accomplished using some other combination of detectors that are properly situated so as to ensure that only diffuse light is detected. A differential measurement of the composite specular and diffuse measurement and the diffuse-only measurement provides a good measure of the specular signal when the specular contribution to the composite signal is large compared to the diffuse contribution. When the specular contribution to the composite signal is small, the difference between the composite signal and the diffuse-only signal can be dominated by the measurements errors of the individual detection elements rather than the magnitude of the specular signal. This effect degrades sensor performance, limiting the usable dynamic sensing range of the sensor.

Utilizing appropriate data processing algorithms, it is possible to examine the detailed measurement of the spatial variations in the light intensity pattern upon the CCD and to locate those detection elements possessing the specular contribution to signal. This technique minimizes the contributions from the diffuse signal to the composite signal, proportionally increasing the contribution of the specular signal, improves sensor accuracy for small specular signals, and extends the practicable dynamic sensing range of the sensor.

Following the storage of the photosite information, microcontroller (MC) 118 executes an algorithm that is stored in ROM 120. The algorithm program, discussed later, serves to decompose the image received from the CCD into the specular flux contribution and the diffuse flux contribution. Finally, the integrated specular and diffuse signal components may be communicated to the master computer using the communications interface 124 via the transmit channel.

V. Data Algorithms

To perform a proper analysis of the data collected from the CCD and stored in the RAM, an algorithm is used. Several types of algorithms may work for the disclosed invention. Specifically, algorithms that have been identified are an object recognition algorithm, a space domain filtering algorithm, or a frequency domain filtering algorithm. Each of these algorithms are discussed below.

With an object-recognition algorithm the waveform is described in some abstract fashion. As an example, if the expected waveform shape is essentially Gaussian, the waveform could be described by parameters $x_0, y_0, d_y, d_x, A_0$, and $B_0$. These six parameters are sufficient to describe a two-dimensional Gaussian waveform of amplitude $A_0$, centered at position $x_0, y_0$ in the image with widths described by $d_y, d_x$ and superimposed upon a baseline signal of amplitude $B_0$. A more complex description would allow rotation of the waveform in the xy-plane. This type of algorithm operates by determining in a best-fit manner, the parameters of the waveform located in the two-dimensional image. Typically the waveform centroid is found by locating the maximum signal amplitude in the two-dimensional image. The algorithm then seeks to determine the best values for all remaining parameters. The algorithm can be made to converge rapidly by providing good initial estimates for some of the waveform parameters. For instance, the widths of the signal should be reasonably well known either from previous measurements or from design principles. Having determined the waveform amplitude, widths, and baseline, it is a simple matter to integrate the signal using either analytical formulae or a look-up table.

With space-domain filtering, the signal is treated as a complex signal with the signal occupying some known band of spatial frequencies. A filter is designed to operate in the spatial domain and implemented as a difference equation. The difference equation is applied to the pixel-by-pixel data in the two-dimensional image to isolate the signal waveform. The filtered signal is then numerically integrated to determine the intensity of the signal in the waveform.

With frequency-domain filtering, the signal is treated as a complex signal with the signal occupying some known band of spatial frequencies. The signal is isolated using a frequency-domain filter after transformation of the two-dimensional image data to the frequency domain using a Fourier or other Z-transform. The intensity of the signal can be determined using either of two methods. The intensity can be determined by direct numerical integration of the signal waveform after applying the inverse transform to the isolated range of frequencies. Alternatively, the signal intensity can be determined directly from the power spectrum of the relevant portion of the frequency spectrum in the frequency domain.

It is to be understood, however, that even through numerous characteristics and advantages of the present invention have been set forth in the foregoing description, together with details of the structure and function of the invention, the disclosure is illustrative, and changes in matters of order, shape, size, and arrangement of parts may be made within the principles of the invention and to the full extent indicated by the broad general meaning of the terms in which the appended claims are expressed.

What is claimed is:

1. A densitometer for measuring optical density of light reflected from an image support member, including:
    signal processing means; and
    a reflectance sensor circuit, coupled to said signal processing means, for receiving the light reflected from said image support member, said reflectance sensor circuit comprising:
    a) means for receiving at least a portion of said reflected light including a plurality of discrete photosites arranged in a matrix array, wherein each of said photosites develops an individual signal proportional to the amount of light received by each of said photosites, said receiving means generating a signal responsive to said received portion of said reflected light;
    b) means for storing said signal generated by said receiving means;
    c) means for actuating said storage means to transmit said stored signal to said signal processing means for analysis thereof.

2. A densitometer according to claim 1, wherein said actuating means comprises an interline transfer architecture having vertical and horizontal output transport registers coupled to said photosites to transmit the individual signals therefrom to said signal processing means for analysis thereof.

3. A densitometer according to claim 2, further including a light source wherein:
    said light source has a de-energized and an energized state; and
    said reflectance sensor circuit includes intensity controlling means for controlling the intensity of said light source during said energized state.

4. A densitometer according to claim 3, wherein said intensity controlling means comprises:
    a) means for producing a first signal from said light source during said energized state; and
    b) means for producing a second signal from said first signal, wherein said second signal adjusts said light source during said deenergized state.

5. A densitometer according to claim 4, wherein said first signal producing means comprises:
    a) a photodiode for receiving said emitted light;
    b) an operational amplifier, receiving an output signal from said photodiode, for creating an amplified signal from said photodiode output signal; and
    c) an analog to digital converter, receiving said amplified output signal from said operational amplifier, for converting said amplified output signal to a corresponding linearly stepping digital signal.

6. A densitometer according to claim 5, wherein said second signal producing means comprises:
    a) a microcontroller receiving an output signal from said analog to digital converter;
    b) a digital to analog converter receiving an output signal from said microcontroller;
    c) a light intensity controller receiving an output signal from said digital to analog converter and said operational amplifier; and
    d) a light intensity drive circuit, for driving the intensity of said light source in response to said light intensity controller.

7. A densitometer according to claim 6, wherein said incident light source comprises a light emitting diode.

8. A densitometer according to claim 1, wherein said signal processing means includes means for processing each of said proportional individual signals transmitted from said actuation means.

9. A densitometer in accordance with claim 8, wherein said signal processing means comprises:
    a) means, responsive to said actuating means, for processing a first signal;
    b) means, responsive to said first processing signal, for processing a second signal comprising at least first and second component signals;
    c) means, responsive to said second processing signal, for processing a third signal to communicate said at least first and second component signals to a main computing system; and
    d) means, responsive to said third processing signal, for processing a fourth signal to coordinate timing of proper energization and de-energization of said light source and for actuating said storage means of said reflectance sensor circuit.

10. A densitometer in accordance with claim 9, wherein said first processing signal means comprises:
a) means for producing amplified linear analog signals in response to said proportional individual signals; and
b) an analog-to-digital converter for converting said amplified linear analog signals into corresponding stepping digital signals.

11. A densitometer in accordance with claim 10, wherein said second processing signal means comprises:
a) means for storing said linearly stepping digital signals; and
b) means for separating said corresponding stepping digital signals into said at least first and second component signals, wherein said first component signal is capable of identifying specularly reflected light and said second component signal is capable of identifying diffusely reflected light.

12. A densitometer according to claim 11, wherein said reflectance sensor is a charge-coupled device.

13. An electrophotographic printing machine adapted to monitor optical density of light reflected from an image support member, including:
means for establishing at least one toner test patch on said image support member; and
a densitometer for measuring said optical density, having:
a light source for emitting light onto said image support member;
signal processing means; and
a reflectance sensor circuit coupled to said signal processing means for receiving the light reflected from said image support member, said reflectance sensor circuit comprising:
a) means for receiving at least a portion of said reflected light including a plurality of discrete photosites arranged in a matrix array, wherein each of said photosites develops an individual signal proportional to the amount of light received by each of said photosites, said receiving means generating a signal responsive to said received portion of said reflected light;
b) means for storing said signal generated by said receiving means;
c) means for actuating said storage means to transmit said stored signal to said signal processing means for analysis thereof.

14. An electrophotographic printing machine according to claim 13, wherein said actuating means comprises an interline transfer architecture having vertical and horizontal output transfer registers coupled to said photosites to transmit the individual signals therefrom to said signal processing means for analysis thereof.

15. An electrophotographic printing machine according to claim 14, wherein:
said light source has a de-energized and energized state; and
said sensor circuitry includes intensity controlling means for controlling the intensity of said light source during said energized state.

16. An electrophotographic printing machine according to claim 15, wherein said intensity controlling means comprises:
a) means for producing a first signal from said light source during said energized state;
b) means for producing a second signal from said first signal,
wherein said second signal adjusts said light source during said de-energized state.

17. An electrophotographic printing machine according to claim 16, wherein said first signal producing means comprises:
a) a photodiode for receiving said emitted light before reflecting off of said photoconductor;
b) an operational amplifier, receiving an output signal from said photodiode, for creating an amplified signal from said photodiode output signal; and
c) an analog to digital converter, receiving said amplified output signal from said operational amplifier, for converting said amplified output signal to a corresponding linearly stepping digital signal.

18. An electrophotographic printing machine according to claim 17, wherein said second signal producing means comprises:
a) a microcontroller receiving an output signal from said analog to digital converter;
b) a digital to analog converter receiving an output signal from said microcontroller;
c) a light intensity controller receiving an output signal from said digital to analog converter and said operational amplifier; and
d) a light intensity drive circuit, for driving the intensity of said light source in response to said light intensity controller.

19. An electrophotographic printing machine according to claim 18, wherein said light source comprises a light emitting diode.

20. A electrophotographic printing machine in accordance with claim 13, wherein said signal processing means further includes means for processing each of said proportional individual signals transmitted from said actuating means.

21. An electrophotographic printing machine in accordance with claim 20, wherein said signal processing means comprises:
a) means, responsive to said actuating means, for processing a first signal;
b) means, responsive to said first processing signal, for processing a second signal comprising at least first and second component signals;
c) means, responsive to said second processing signal, for processing a third signal to communicate said at least first and second component signals to a main computing system; and
d) means, responsive to said third processing signal, for processing a fourth signal to coordinate timing of proper energization and de-energization of said light source and for actuating said storage means of said reflectance sensor circuit.

22. An electrophotographic printing machine in accordance with claim 21, wherein said first processing signal means comprises:
a) means for producing amplified linear analog signals in response to said proportional individual signals; and
b) an analog-to-digital converter for converting said amplified linear analog signals into corresponding stepping digital signals.

23. An electrophotographic printing machine in accordance with claim 22, wherein said second processing signal means comprises:
a) means for storing said linearly stepping digital signals; and b) means for separating said corresponding stepping digital signals into said at least first and second component signals, wherein said first component signal is capable of identifying specularly reflected light and said second component signal is capable of identifying diffusely reflected light.

24. An electrophotographic printing machine according to claim 23, wherein said reflectance sensor is a charge-coupled device.

25. A method of measuring reflected light from a light source, including the steps of:
   a) receiving at least a portion of said reflected light, wherein said receiving step comprises the steps of providing a plurality of discrete photosites arranged in a matrix array, and developing an individual signal at each photosites proportional to the amount of light received by each of said photosites;
   b) storing said signal generated in said receiving step into a storage means;
   c) actuating said storage means to transmit said signal therefrom; and
   d) processing said transmitted signal from said actuating step for analysis thereof.

26. A method of measuring reflected light according to claim 25, wherein said actuating step comprises transferring said proportional individual signals away from said plurality of photosites by an interline transfer architecture having vertical and horizontal output transport registers.

27. A method of measuring reflected light according to claim 26, wherein said receiving step comprises:
   a) energizing and de-energizing sai light source; and
   b) controlling the intensity of said light source during said energizing.

28. A method of measuring reflected light according to claim 27, wherein said intensity controlling step comprises:
   a) producing a first signal from said light source during said energized state before said light reflects off said member;
   b) producing a second signal from said first signal, wherein said second signal adjusts said light source during said de-energized state.

29. A method of measuring reflected light according to claim 28, wherein said first signal producing step comprises:
   a) receiving said emitted light, before being reflecting off of said member, with a photodiode;
   b) propagating an output signal from said photodiode;
   c) creating an amplified output signal, with an operational amplifier, from said output signal from said photodiode; and
   c) converting said amplified output signal to a corresponding linearly stepping digital signal using an analog to digital converter.

30. A method of measuring reflected light according to claim 29, wherein said second signal producing step comprises:
   a) receiving said digital signal with a microcontroller;
   b) generating a microcontroller signal responsive to said digital signal;
   c) converting said microcontroller signal to an analog signal using a digital to analog converter;
   c) collecting said analog signal and said amplified output signal with a light intensity controller;
   d) propagating a light intensity signal from said light intensity controller; and
   d) pulsing said light source in response to said light intensity signal.

31. A method of measuring reflected light in accordance with claim 25, further including the step of processing said proportional individual signals, from said actuating step, for communicating said processed proportional individual signals with a main computing system in response to a signal processing means.

32. A method of measuring reflected light in accordance with claim 31, wherein said processing step comprises:
   a) generating a first processing signal, responsive to said signal from said actuating step;
   b) initiating a second processing signal, responsive to said first processing signal, comprising at least two component signals;
   c) propogating a third processing signal, responsive to said second processing signal, for communicating said at least two component signals to a main computing system; and
   d) creating a fourth processing signal, responsive to said third processing signal, for coordinating timing of proper activation of a light source and a reflectance sensor.

33. A method of measuring reflected light in accordance with claim 32, wherein said first processing step comprises the steps of:
   a) producing amplified linear analog signals in response to said proportional individual signals; and
   b) converting said amplified linear analog signals into corresponding stepping digital signals.

34. A method of measuring reflected light in accordance with claim 33, wherein said propagating a second processing signal comprises the steps of:
   a) storing said linearly stepping digital signals; and
   b) separating said corresponding stepping digital signals into said at least first and second component signals, wherein said first component signal is capable of identifying specularly reflected light and said second component signal is capable of identifying diffusely reflected light.

* * * * *